United States Patent
Lee et al.

(10) Patent No.: US 7,497,831 B2
(45) Date of Patent: Mar. 3, 2009

(54) BLOOD PRESSURE MEASURING SYSTEM AND METHOD

(75) Inventors: Jong-youn Lee, Yongin-si (KR); Hye-jin Jung, Seoul (KR); Kyung-ho Kim, Yongsin-si (KR)

(73) Assignee: Samsung Electronics Co., Ltd., Suwon-si, Gyeonggi-doo ( * ) Notice: Subject to any disclaimer, the term of this patent is extended or adjusted under 35 U.S.C. 154(b) by 244 days.

(21) Appl. No.: 11/150,467

(22) Filed: Jun. 13, 2005

(65) Prior Publication Data
US 2005/0283083 A1 Dec. 22, 2005

(30) Foreign Application Priority Data
Jun. 11, 2004 (KR) .................... 10-2004-0043070

(51) Int. Cl.
*A61B 5/02* (2006.01)
(52) U.S. Cl. .................. 600/490; 600/485; 600/500; 600/504
(58) Field of Classification Search .............. 600/485, 600/490, 500, 504
See application file for complete search history.

(56) References Cited

U.S. PATENT DOCUMENTS

| | | | | | |
|---|---|---|---|---|---|
| 3,051,165 | A | * | 8/1962 | Kompelien | 600/480 |
| 3,920,004 | A | * | 11/1975 | Nakayama | 600/493 |
| 4,343,314 | A | * | 8/1982 | Sramek | 600/493 |
| 4,730,621 | A | * | 3/1988 | Stott | 600/480 |
| 4,846,189 | A | | 7/1989 | Sun | |
| 5,072,736 | A | * | 12/1991 | Ogawa et al. | 600/493 |
| 2006/0253041 | A1 | * | 11/2006 | Shin et al. | 600/493 |

OTHER PUBLICATIONS

Santic, Ante, et al., "Simultaneous Application of Multiple Oscillometric Methods for Blood Pressure Measurement in Finger", Proceedings of The First Joint BMES/EMBS Conference Serving Humanity, Advancing Technology Oct. 13-16, 1999, Atlanta, GA, USA, p. 231 [copyright 1999—IEEE].

* cited by examiner

*Primary Examiner*—Robert L Nasser
*Assistant Examiner*—Karen E Toth
(74) *Attorney, Agent, or Firm*—Lee & Morse, P.C.

(57) ABSTRACT

A blood pressure measuring system and method are provided. The blood pressure measuring system includes a first sensing unit sensing a patient's blood pressure, a second sensing unit sensing a patient's blood flow, a pressure control unit controlling a pressure applied to the patient by the first sensing unit, and an operation and control unit controlling an operation of the pressure control unit and calculating a patient's blood pressure by analyzing and comparing signals output from the first and second sensing units.

19 Claims, 6 Drawing Sheets

BLOOD PRESSURE MEASURING SYSTEM AND METHOD

BACKGROUND OF THE INVENTION

1. Field of the Invention

The present invention relates to a system and method of measuring physiological signals of the human body, and more particularly, to a blood pressure measuring system and method.

2. Description of the Related Art

Physiological signals of a human body include information which can help in diagnosing the health of the human body. One such physiological signal is blood pressure, which, from a medical point of view, may be indicative of disorders of the circulatory system. When blood pressure is abnormal, an appropriate remedy may be taken after determining the cause of the abnormality.

Blood pressure can be classified into systolic pressure and diastolic pressure. The systolic pressure is measured when the heart ventricles contract, and the diastolic pressure is measured when the heart ventricles relax. When the heart ventricles relax, blood is not transported to arteries. Nevertheless, due to elasticity of the walls of blood vessels, blood inside the blood vessels is pressed somewhat, even though the degree of pressing is less than when the ventricle contracts. Accordingly, the diastolic pressure does not become zero.

Blood pressure may change depending on a variety of factors including, e.g., a patient's psychological state, measuring conditions, the environment, etc. For example, when a doctor or a nurse measures the patient's blood pressure, the patient's blood pressure may rise due to tension. Thus, it may be difficult to accurately measure the patient's blood pressure using only one measurement. Blood pressure measured when the patient has an empty stomach, just after getting up in the morning, may be referred to as the basal blood pressure, and may be very helpful for diagnosis. However, it may be troublesome to measure the basal blood pressure in real life. Medical centers, such as hospitals, may have difficulty assuring the conditions under which the basal blood pressure is to be measured, e.g., it may be difficult for the medical center to schedule patients early in the morning. The conditions under which the basal blood pressure is to be measured may be more easily met at home.

Various portable electronic blood pressure measuring devices, known as sphygmomanometers, have been developed and may be used in the home by the patient. Automated electronic sphygmomanometers capable of indirectly measuring the blood pressure have recently been developed. One type, hereinafter referred to as a conventional sphygmomanometer, employs a volume-oscillometric method to indirectly measure the blood pressure. Unlike auscultatory, or audible, sphygmomanometers, measurements made with a volume-oscillometric sphygmomanometer need not rely on a special converter or microphone.

FIG. 1 illustrates graphs of signals derived from a blood pressure measurement made using a conventional sphygmomanometer. A pressure signal G1 may be measured in a pressure cuff as a pressure applied to the cuff is reduced. Typically, the pressure cuff will be wrapped around an appendage, e.g., an arm, of a patient. An oscillating waveform G2, extracted from the pressure signal G1, represents pressure changes in the cuff related to pressure changes in an artery beneath the cuff, and is indicative of a pulse wave of the patient's blood pressure. The oscillating waveform G2 may be obtained from the pressure signal G1 by passing the pressure signal G1 through a 0.5 Hz high-pass filter. The volume-oscillometric method indirectly measures blood pressure by analyzing changes in the oscillating waveform G2, and uses that analysis to determine which points in the pressure signal G1 represent the patient's systolic and diastolic blood pressures.

Oscillations in the oscillating waveform G2 first appear when pressure in the cuff, represented by the declining pressure signal in graph G1, first drops below the patient's systolic blood pressure. At this point, the pressure in the cuff has decreased to the point where the patient's blood can begin to flow and pressure variations in the cuff caused by systolic pressure become evident.

It can be seen that the oscillating waveform G2 eventually reaches a maximum amplitude, which is indicative of the mean blood pressure MP. This value is generally easy to determine. In contrast to measurements made by the auscultatory method, however, it is more difficult to determine the systolic and diastolic blood pressures from the oscillating waveform G2. In particular, as the systolic pressure is indicated by the point at which oscillations first appear, the oscillating signal may be quite small at that point. Thus, automatically determining the point at which oscillations first appear may be difficult. In particular, noise in the signal may produce an error in determining where the oscillations first appear, which, in turn, may produce an error in determining what value in the pressure signal G1 represents the patient's systolic blood pressure.

Since the maximum amplitude in the oscillating waveform G2, the mean blood pressure MP, is generally easier to determine than the point at which oscillations first appear, the oscillometric method typically determines the systolic and diastolic pressures based on the mean blood pressure MP. Constant ratios are assumed between the value of the maximum oscillation in the oscillating waveform G2 and the values of the oscillations occurring in at the systolic pressure and the diastolic pressures, respectively. These ratios will be referred to as characteristic ratios. Thus, the volume-oscillometric method involves determining a maximum value of the oscillating waveform G2 and estimating the systolic and diastolic pressures based on the maximum value by applying the characteristic ratios to the maximum value. Tests have shown that the point in the oscillating waveform G2 that is representative of the systolic blood pressure corresponds to about 50% of the maximum oscillation, and the point in the oscillating waveform G2 that is representative of the diastolic blood pressure corresponds to about 50-80% of the maximum oscillation. Thus, a ratio of the systolic blood pressure SBP to the mean blood pressure MP and a ratio of the diastolic blood pressure to the mean blood pressure MP are the characteristic ratios.

In other words, the cuff pressure may be determined to be the systolic pressure where the amplitude SBP corresponds to 50% of the maximum amplitude MP. Similarly, the cuff pressure may be determined to be the diastolic pressure where the amplitude (not shown) corresponds to 75% of the maximum amplitude MP.

Unfortunately, the characteristic ratios may differ by 10-20% depending on differing body and biological characteristics of the patients and the cuffs used, e.g., differing external shapes of the cuffs, differing elasticity of the cuffs, differing pressure transfer characteristics in the patients' arteries or arms, differing viscosity and elasticity characteristics in the walls of arterial vessels, differing shapes and amplitudes of the blood pressure waveform of the heart artery, etc. Additionally, as the conventional sphygmomanometer measures the blood pressure at an upper arm, the patient may need to take off an upper garment and, since a large pressure may be applied to the arm of the patient, the patient may feel pain during repeated measurements.

A sphygmomanometer that can measure the blood pressure through a finger has been developed. Using the finger sphygmomanometer, the signals may be measured at an artery of the finger, which will typically be narrower than that of an upper arm. A signal-to-noise (S/N) ratio may be low and motion of the finger may have a great influence on the signals. Also, due to the difference in the transfer characteristic of the circulatory system, the blood pressure measured at the peripheral artery may be different from that measured at the upper arm. Accordingly, there is a need for an improved approach to measuring blood pressure.

SUMMARY OF THE INVENTION

The present invention is therefore directed to a blood pressure measuring system and method, which substantially overcome one or more of the problems due to the limitations and disadvantages of the related art.

It is therefore a feature of an embodiment of the present invention to provide a blood pressure measuring system that includes a blood flow sensor.

It is therefore another feature of an embodiment of the present invention to provide a method for measuring blood pressure that includes determining blood pressure using information provided by a blood flow sensor.

At least one of the above and other features and advantages of the present invention may be realized by providing . . .

BRIEF DESCRIPTION OF THE DRAWINGS

The above and other features and advantages of the present invention will become more apparent to those of ordinary skill in the art by describing in detail exemplary embodiments thereof with reference to the attached drawings in which.

DETAILED DESCRIPTION OF THE INVENTION

Korean Patent Application No. 10-2004-0043070, filed on Jun. 11, 2004, in the Korean Intellectual Property Office, and entitled: "BLOOD PRESSURE MEASURING SYSTEM AND METHOD," is incorporated by reference herein in its entirety The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. In the figures, the dimensions of layers and regions are exaggerated for clarity of illustration.

First, a blood pressure measuring system according to an embodiment of the present invention will be described. A cuff, acting as a pressure sensing unit, may be placed at a base of a finger and a blood flow sensing unit may be placed on an end of the finger to sense blood flow. A patient's blood pressure may be measured by analyzing and comparing a signal corresponding to blood pressure to a signal corresponding to blood flow.

Figure 2:
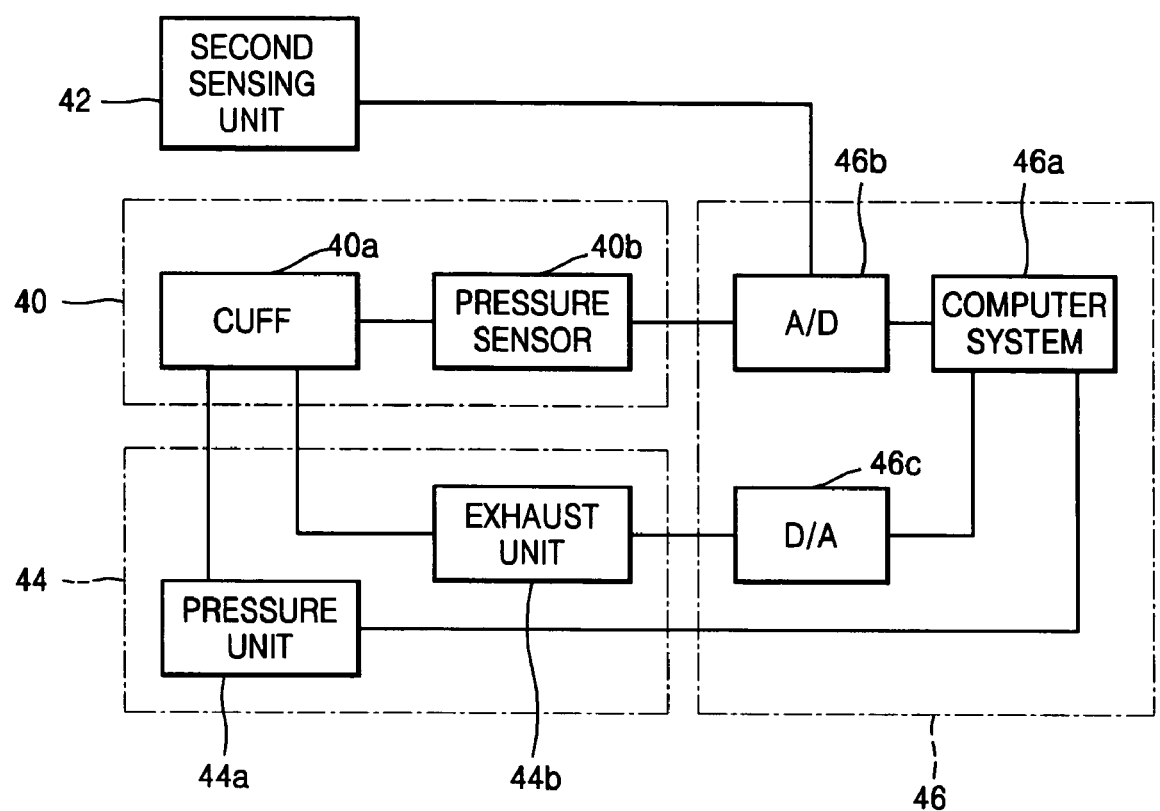
FIG. 2 illustrates a block diagram of a blood pressure measuring system according to an embodiment of the present invention.

FIG. 2 illustrates a block diagram of a blood pressure measuring system according to an embodiment of the present invention. The blood pressure measuring system may include a first sensing unit 40 for sensing a pressure, a second sensing unit 42 for sensing a patient's blood flow, a pressure control unit 44 and an operation and control unit 46.

The first sensing unit 40 may include a device 40a, placed on a part of a patient's body, and a pressure sensor 40b, sensing a pressure. The device 40a may be a pressure cuff placed at the base of the finger. The pressure control unit 44 may include a pressure unit 44a and an exhaust unit 44b. The operation and control unit 46 may include an analog-to-digital converter 46b, a digital-to-analog converter 46c and a computer system 46a. The computer system 46a may analyze and process the signals output from the first and second sensing units 40 and 42, display a blood pressure measured based on the analyzed and processed signals and control the pressure control unit 44.

In measuring blood pressure, a pressure higher than the systolic pressure may be applied to the cuff 40a of the first sensing unit 40. For this purpose, the pressure unit 44a may include a pump that supplies a liquid or a gas, e.g., air, at a predetermined pressure to the cuff 40a. It is preferable that the pressure applied by the cuff 40a to the patient does not exceed 300 mmHg. The pressure unit 44a may supply air to the cuff until the cuff pressure becomes higher than the systolic pressure. The pressure sensor 40b may be a transducer to sense the cuff pressure and convert it into an electrical signal. The pressure sensor 40b may be built in the cuff 40a or may be independently provided outside the cuff 40a.

The analog-to-digital converter 46b of the operation and control unit 46 may convert an analog signal from the pressure sensor 40b into a digital signal. The computer system 46a may analyze and process the digital signal and transfer control signals to the digital-to-analog converter 46b, so as to control the pressure control unit 44. The digital-to-analog converter 46c may convert the control signals into signals that are output to control the pressure control unit 44. For example, when the digital signals from the analog-to-digital converter 46b are analyzed and processed, if the cuff pressure is more than 300 mmHg, an operation of the pressure unit 44a may be stopped. Simultaneously, a signal for reducing the cuff pressure may be applied to the digital-to-analog converter 46c to convert it to analog signal. The analog signal may be output from the digital-to-analog converter 46c to the exhaust unit 44b, which may include a proportional control valve. The exhaust unit 44b may exhaust air from the cuff according to the control signal provided from the operation and control unit 46. The cuff pressure may be reduced linearly or nonlinearly. The former case is a normal blood pressure measuring process, and the air may be slowly exhausted until the cuff pressure becomes lower than the systolic pressure. The latter case may occur if the cuff pressure exceeds a predetermined pressure, for example 300 mmHg, which may cause pain in the patient. Thus, the cuff pressure may be rapidly reduced by momentarily exhausting the air from the cuff 40*a*.

These operations of the exhaust unit 44*b* may be continued until a stop signal is supplied from the operation and control unit 46. In this manner, the operation and control unit 46 may control the pressure unit 44 so that the cuff pressure may be properly maintained during blood pressure measurement.

The second sensing unit 42 may be disposed spaced apart from the first sensing unit 40, e.g., by a predetermined distance. The first sensing unit 40 may be placed at the base of the finger and the second sensing unit 42 may be placed on the end of the finger. The second sensing unit 42 may include an optical sensor, pneumatic device or electrical device to detect a degree of expansion or optical absorption of a blood vessel and measure blood flow in the blood vessel. The signal output from the second sensing unit 42 may be transferred to the computer system 46*a* through the analog-to-digital converter 46*b*. The computer system 46*a* may analyze and process a volume oscillometric signal extracted from the pressure signal of the first sensing unit 40 in connection with the signal from the second sensing unit 42. That is, the computer system 46*a* may analyze and process the pulse wave of the blood pressure in view of the blood flow signal from the second sensing unit 42 to measure the systolic pressure, the diastolic pressure and the mean blood pressure of the patient according to the method of the present invention disclosed herein. The computer system 46*a* may perform compensation operations, e.g., shifting a signal, while analyzing and processing the pulse wave of the blood pressure and the blood flow changing signal, and may display the results for the patient to view.

Figure 3:
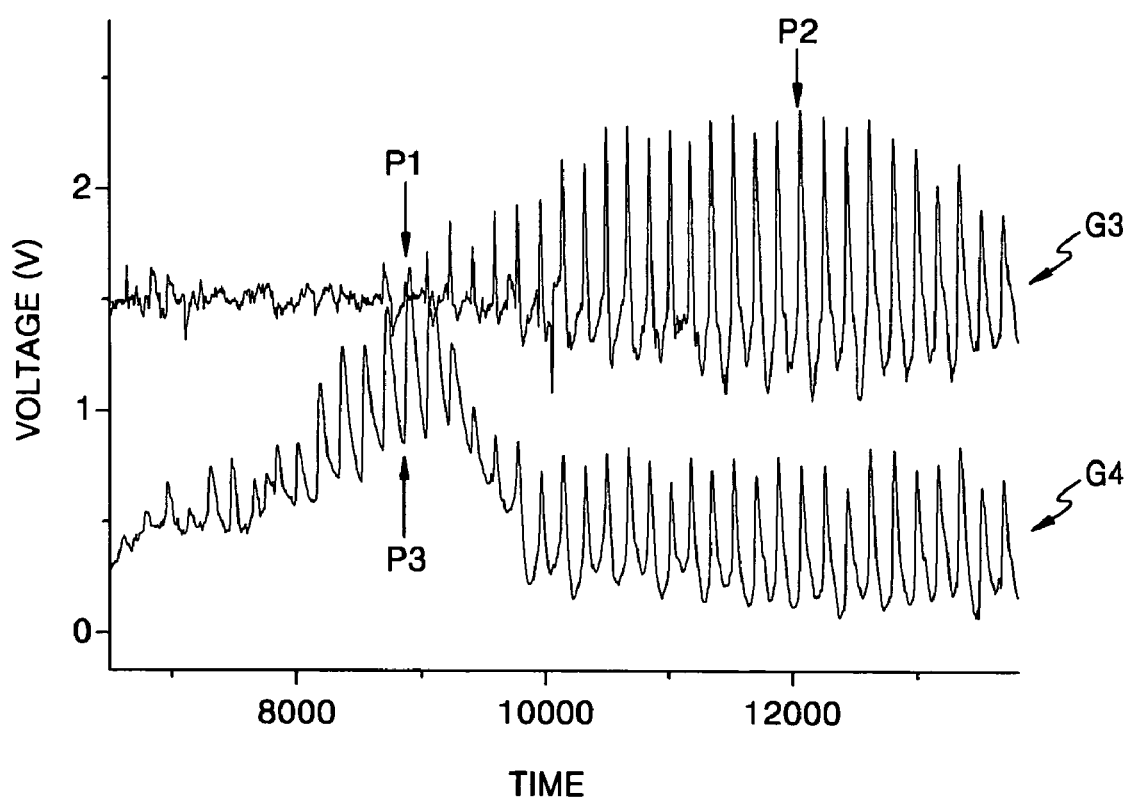
FIG. 3 illustrates changes in a blood pressure and a blood flow, according to the blood pressure measuring system of FIG. 2.

FIG. 3 illustrates signals corresponding to blood pressure and blood flow, according to the blood pressure measuring system of FIG. 2. Graph G3 represents a pulse wave of blood pressure from the first sensing unit 40, and graph G4 represents a blood flow signal from the second sensing unit 42. Point P1 in the graph G3 indicates a first appearance of oscillations, corresponding to a significant pulse wave occurring at the point at which the cuff pressure becomes lower than the systolic pressure. A point P2 in the graph G3 indicates the mean pressure. Point P3 in the graph G4 indicates a maximum value in the blood flow signal and coincides with the point P1, which may be explained as set forth below.

During the normal blood pressure measuring process, the blood does not flow to the end of the finger while the cuff pressure is higher than the systolic pressure, but it begins to flow there once the cuff pressure becomes lower than the systolic pressure. The change in the blood flow at the end portion of the finger is at a maximum at the point P1. Thereafter, the blood begins to circulate through the base of the finger as the cuff pressure is reduced, and the blood flow at the end of the finger begins to decrease, as illustrated by the declining signal to the right side of the point P3. The shapes of graphs G3 and G4 may change depending on the patients. However, changes in blood pressure and blood flow with respect to the same patient are generally correlated. Accordingly, the fact that the point P1 and the point P3 in the graph G4 coincides is common to all patients if the blood pressure is measured in a normal state. Thus, the blood flow measured at the end of the finger may be used as an index in the measurement of the patient's blood pressure, i.e., as an index to the point at which the patient's systolic pressure occurs.

Figure 4:
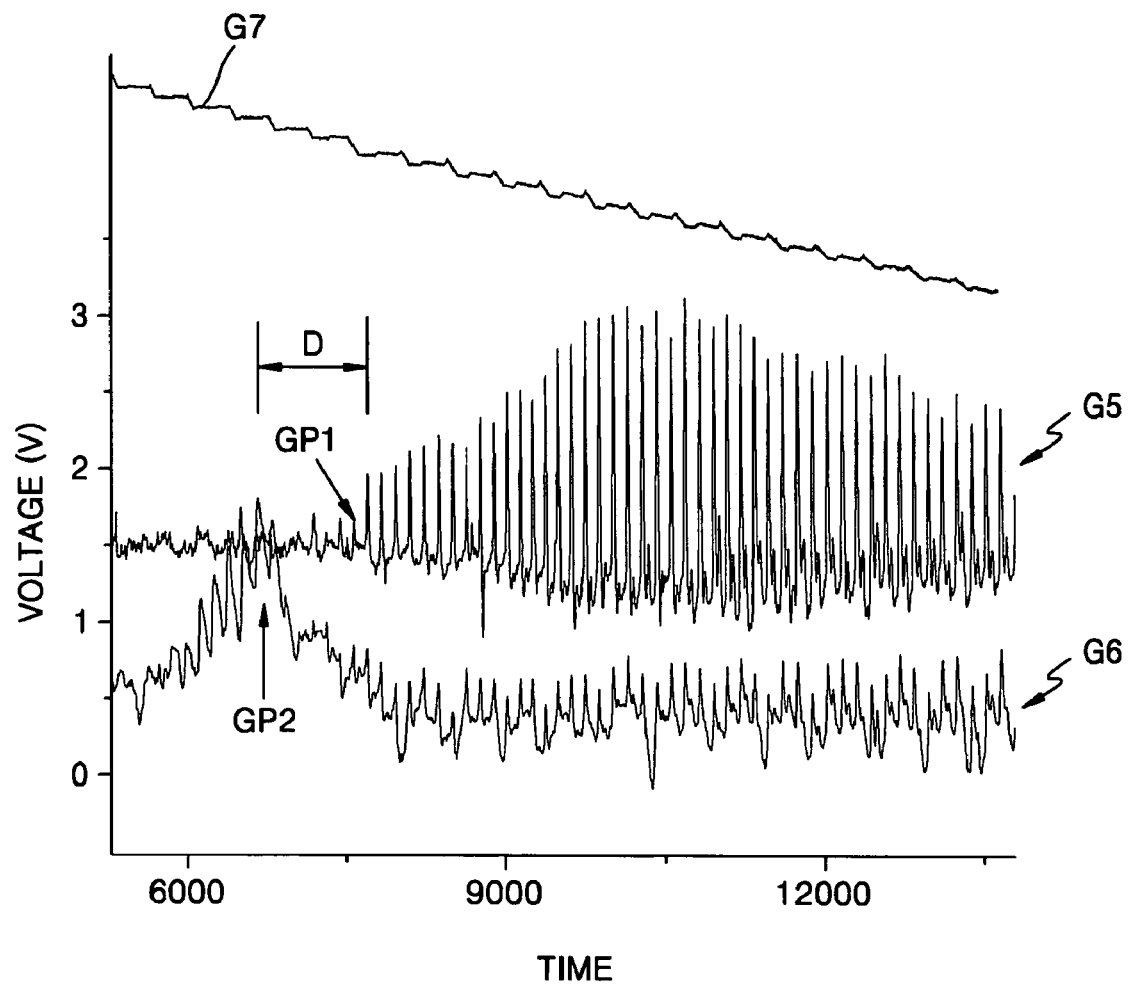
FIG. 4 illustrates mismatching between a blood pressure signal and a blood flow signal.

Due to a transfer characteristic of the patient's blood vessel, inflection points of the change in the blood flow measured at the end of the finger may not be identical. That is, the systolic pressures may not be identical between the graph illustrating the blood pressure change and the graph illustrating the oscillating waveform of the pulse wave of the blood pressure (i.e., the volume oscillometric signal). FIG. 4 illustrates mismatching between a blood pressure signal and a blood flow signal. Graph G5 represents the blood pressure signal provided by the first sensing unit 40, and a graph G6 represents the blood flow signal provided by the second sensing unit 42. In a similar fashion to that described above in connection with FIG. 1, the waveform of the blood pressure signal G5 in FIG. 4 may be obtained by filtering a cuff pressure signal G7. A point GP2, when a maximum peak appears in the blood flow signal, may not coincide with a point GP1, when an oscillation in the blood pressure signal first appears. Compared with the point GP2, the point GP1 may be offset by an amount D. It is apparent that, absent the indexing provided by the sensing of blood flow, a determination of the patient's blood pressure might be in error by an amount corresponding to amount D.

In this case, the point GP2 may be used as an index. In an embodiment, the point GP1 and the point GP2 may be matched by left-shifting the blood pressure signal G5 with respect to the point GP2, so that the blood pressure and blood flow readings coincide. Thereafter, the blood pressure may be determined. In particular, the waveform of the blood pressure signal G5 may be analyzed, e.g., using the volume-oscillometric method, to determine the point in the waveform that represents the maximum (mean blood pressure) and, based on the characteristic ratios, the points in the waveform representing the systolic and diastolic pressures may be determined. In contrast to the conventional method, however, these pressures may then adjusted or corrected, in view of the blood flow signal, by shifting the pressure signal G5 with respect to the cuff pressure signal. That is, the waveform of the pressure signal G5 may be shifted with respect to the cuff pressure signal from which the waveform was extracted.

Figure 1:
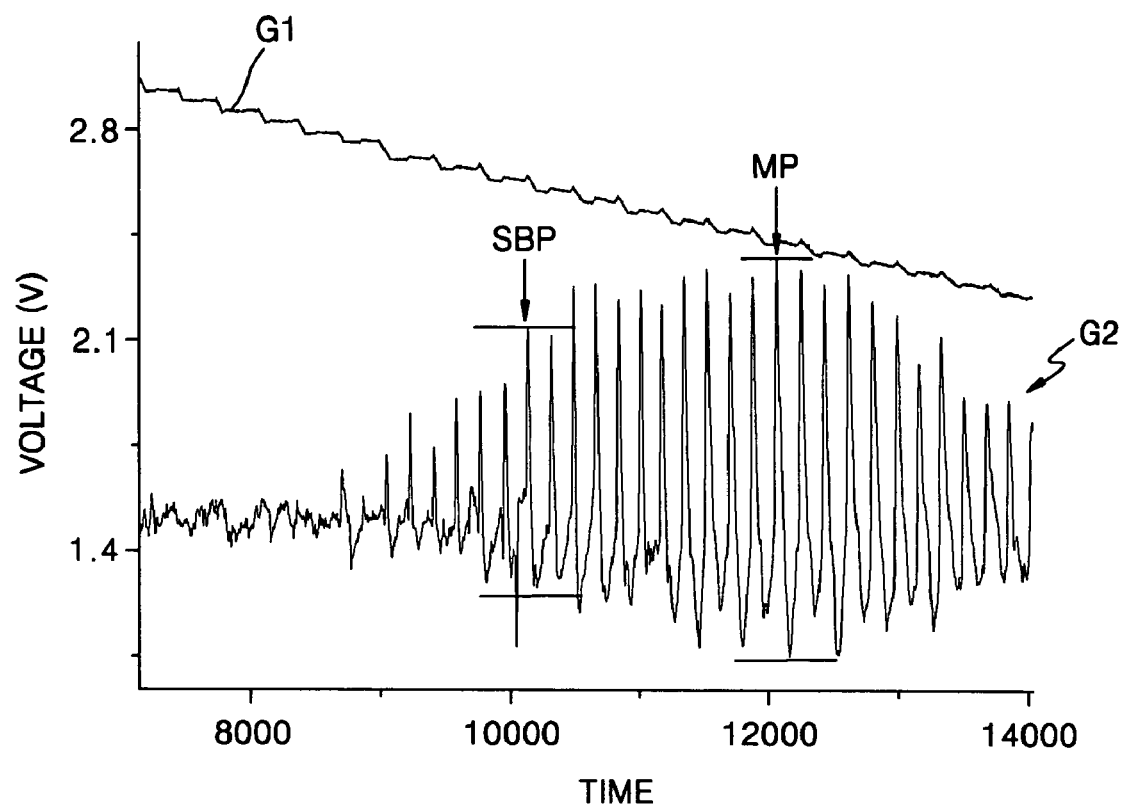
FIG. 1 illustrates graphs of electrical signals measured when blood pressure is measured using a conventional sphygmomanometer.

With reference to the conventional method, the results of which are illustrated in FIG. 1, the present invention may provide additional accuracy. In FIG. 1, the waveform of the blood pressure signal G2 is obtained by filtering the cuff pressure signal G1. Conventionally, the waveform of the blood pressure signal G2 is analyzed by the volume-oscillometric method to determine the points in the waveform that represent maximum (mean blood pressure MP), the systolic pressure SBP and the diastolic pressure (not shown). Those points are then directly related with the pressure values in the cuff pressure signal G1. Thus, for the point SBP, the conventional method would calculate the systolic blood pressure to be equal to the cuff pressure that was measured at about 10,000 on the time scale. In contrast, according to this embodiment of the present invention, the indexing feature provided by sensing blood flow would allow for the waveform of the blood pressure signal G2 to be left-shifted with respect the cuff pressure signal G1. Accordingly, in a hypothetical example, the point SBP might be left shifted so that the systolic blood pressure SBP correlates with the cuff pressure that was measured at about 9,500 on the time scale.

A method for measuring blood pressure using the system of the present invention will now be described according to an embodiment of the present invention. Procedures for placing the sensing units on the patient's body are omitted. Sensing units having various shapes may be used as the pressure sensing unit and the blood flow sensing unit, and the sensing units may be placed on various parts of the patient's body. In an embodiment, the pressure sensing unit and the blood flow sensing unit may be placed at the base and the end of the finger, respectively. A cuff with a built-in pressure sensor may be used as the pressure sensing unit and an optical sensor may be used as the blood flow sensing unit.

Figure 5:
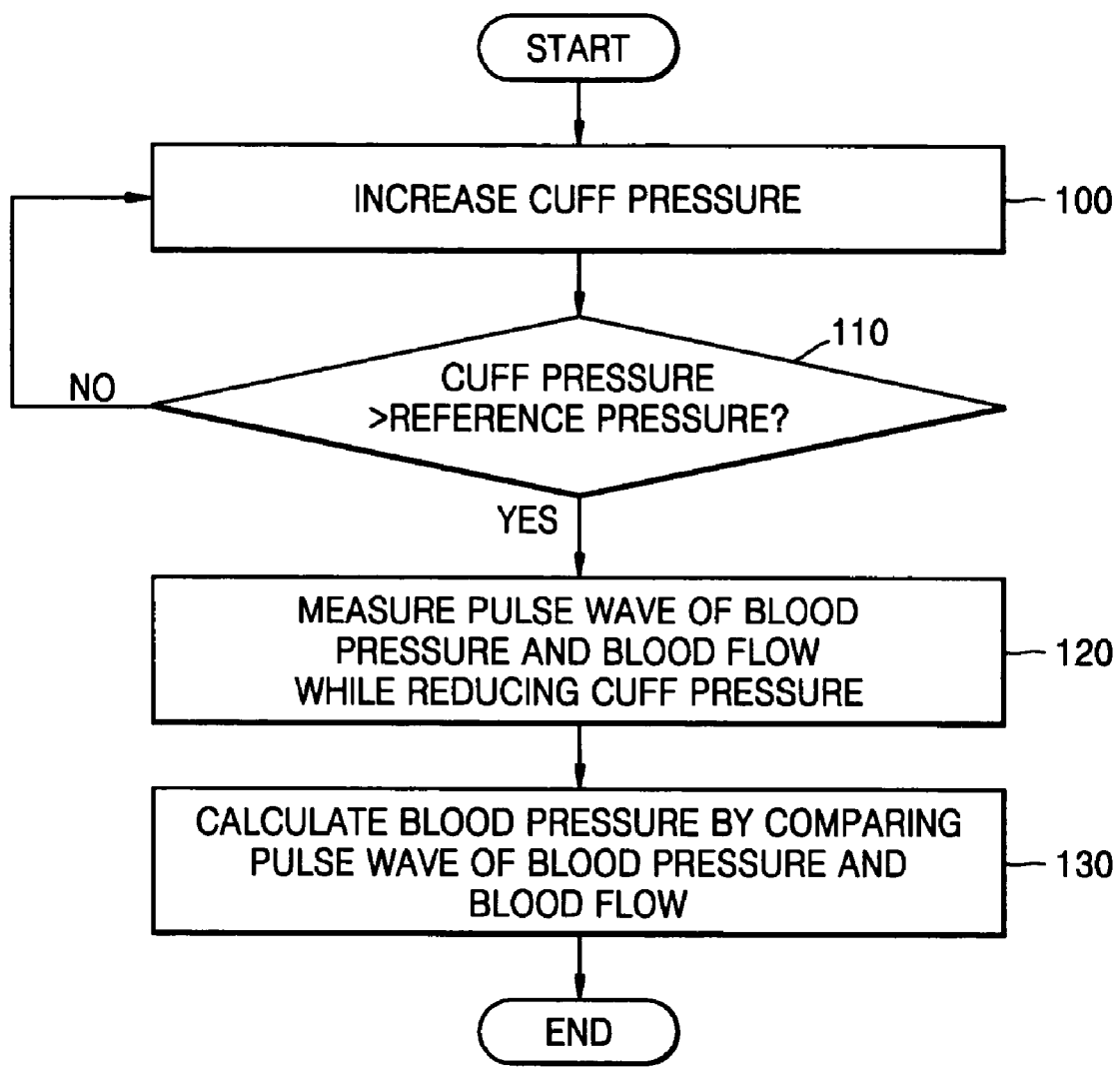
FIG. 5 illustrates a method of measuring a blood pressure according to an embodiment of the present invention.

Referring to FIGS. 2 and 5, in operation 100, the cuff pressure may be increased to a predetermined point using the pressure unit 44a of the pressure control unit 44, which may be connected to the cuff 40a. In operation 110, the cuff pressure may be compared with a stored reference pressure (e.g., an empirical value corresponding to a maximum estimated systolic pressure) using the computer system 46a of the operation and control unit 46. It is preferable that the cuff pressure not exceed 300 mmHg. If the cuff pressure is larger than the reference pressure, the process may proceed to operation 120. If not, the process may continue to perform the operations 100 and 110 until the reference cuff pressure is attained.

In operation 120, the cuff pressure may be sensed, the pulse wave of the finger's blood pressure detected and the change in the blood flow at the end of the finger detected as the cuff pressure is reduced. Detecting the pulse wave of the finger's blood pressure may include sensing the cuff pressure signal as the cuff pressure is reduced and filtering the pressure signal using, e.g., a 0.5 Hz high-pass filter and/or other filters, which may be implemented in hardware, in software installed in the computer system 46a, etc. The pulse wave of the finger's blood pressure may be extracted during the filtering operation. The cuff pressure signal may be sensed using a pressure sensor that may be built into the cuff or separately provided. Those skilled in the art will appreciate that the above operations may be similarly done as the cuff pressure is increased from a point below the diastolic pressure.

In operation 130, the blood pressure may be calculated by comparing the pulse wave of the blood pressure with the blood flow. The blood pressure signal may be indexed according to the point at which the maximum blood flow is detected, and the blood pressure may then be determined based on that point. The operation 130 may be divided into detailed operations, as shown in FIG. 6.

Figure 6:
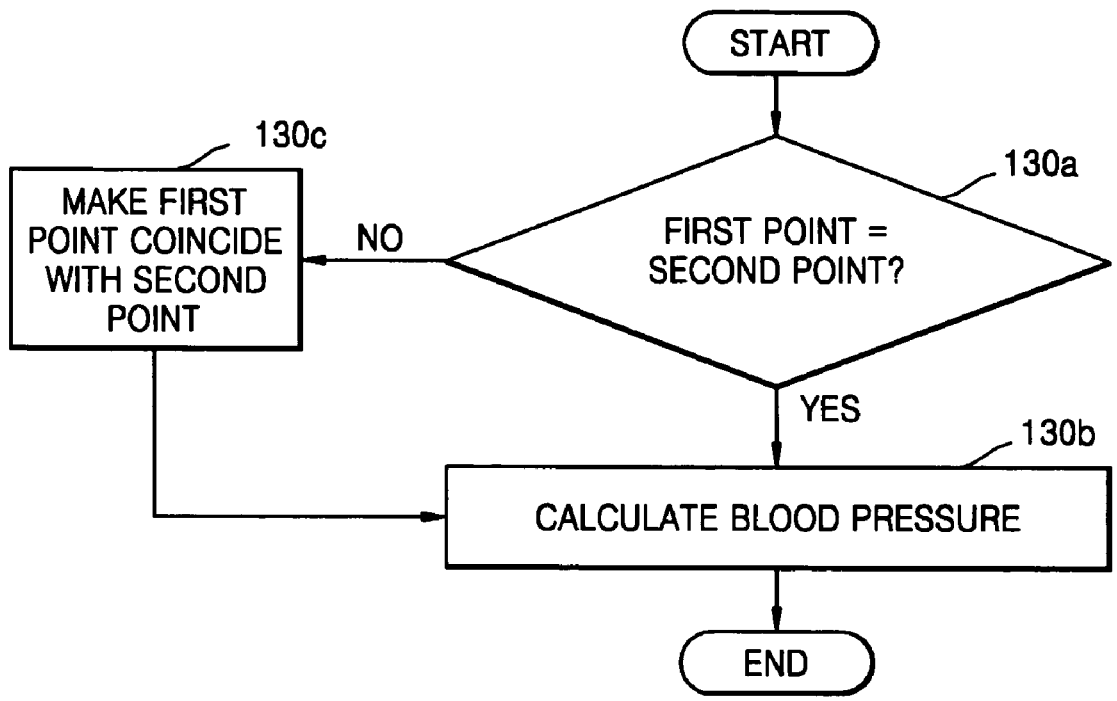
FIG. 6 illustrates details of a method of measuring a blood pressure according to an embodiment of the present invention.

Referring to FIG. 6, in operation 130a, the point corresponding to the systolic pressure (first point), as determined by the volume-oscillometric method, may be checked against the point corresponding to the maximum peak in the blood flow (second point). In operation 130b, if the first point coincides with the second point, the blood pressure may be directly determined using the volume-oscillometric method.

In operation 130c, if the first point does not coincide with the second point, a compensation process may be performed to adjust the first point until it coincides with the second point. For example, the waveform of the blood pressure pulse wave may be shifted until the first point coincides with the second point. Thereafter, the blood pressure may be determined using the oscillometric method by directly correlating the shifted waveform of the blood pressure pulse wave with the cuff pressure. Those skilled in the art will appreciate that the first and second points may be time points or any other suitable measure by which the two signals may be compared.

In an alternative implementation (not shown), the systolic blood pressure may be determined by directly comparing the blood flow signal to the cuff pressure, in which case the systolic blood pressure may be derived from the maximum blood flow and the cuff pressure without using the characteristic ratio. The diastolic blood pressure may similarly be determined based on the detected maximum in the blood flow signal, or by conventional methods, or by a combination of the two.

EXPERIMENTAL EXAMPLE

Eight patients' blood pressures were measured. In this test, an auscultation method was used as the conventional method. Table 1 shows the test results.

TABLE 1

| Patient | Conventional Method | | The Present Invention | |
|---|---|---|---|---|
| | Systole | Diastole | Systole | Diastole |
| 1 | 0.33 | 3.33 | 4.33 | 6.67 |
| 2 | 2.00 | 2.33 | 2.00 | 2.33 |
| 3 | 1.67 | 1.17 | 10.33 | 1.83 |
| 4 | 2.67 | 9.50 | 7.33 | 2.50 |
| 5 | 1.67 | 1.67 | 1.33 | 3.67 |
| 6 | 2.67 | 3.83 | 3.33 | 1.50 |
| 7 | 1.33 | 1.00 | 7.00 | 3.67 |
| 8 | 1.67 | 6.00 | 1.00 | 2.67 |
| Mean Error (mmHg) | 1.75 | 3.60 | 4.58 | 3.10 |

Referring to Table 1, the mean error in measurements made according to the present invention may be less than ±5 mmHg, a value specified by some specifications relating to electronic medical equipment. Therefore, in accordance with the present invention, satisfactory automated blood pressure detection may be realized measuring a peripheral artery.

The blood pressure measuring system according to the present invention may include a pressure sensing unit for sensing the blood pressure and a blood flow sensing unit for sensing the blood flow. The units may be placed on the patient's body at locations that are proximate or continuous with respect to a blood flow path. A maximum blood flow sensed by the blood flow sensing unit may be used as an index in correctly determining the point at which the systolic pressure occurs in the pulse wave of the blood pressure waveform, such that the systolic pressure, the diastolic pressure and the mean pressure may be more accurately measured. As the blood flow may be used as an index in measuring the blood pressure, a patient's blood pressure may be more accurately measured, even under the influence of confounding factors such as motion, etc.

The present invention provides a blood pressure measuring system that may help minimize an influence of a finger's motion and may also help minimize a difference between a blood pressure measured at a peripheral artery and a blood pressure measured at the heart or upper arm, which results from a difference in the transfer characteristics of the circulatory system.

The scope of the invention is not confined to the details set forth above, and other variations may be implemented without departing from the scope of the invention. For example, the pressure unit 44a and the exhaust unit 44b may be integrally formed, the pressure unit 44a may be configured to supply air to the cuff and exhaust the air out of the pressure unit 44a, the analog-to-digital converter 46b and the digital-to-analog converter 46c may be integrally formed, etc.

Exemplary embodiments of the present invention have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A blood pressure measuring system, comprising:
   a first sensing unit to apply a pressure and to provide a first signal corresponding to a blood pressure of a patient;
   a second sensing unit to provide a second signal corresponding to a blood flow of the patient;
   a pressure control unit to control the pressure applied by the first sensing unit; and
   an operation and control unit, wherein the operation and control unit is adapted to:
      control an operation of the pressure control unit,
      determine the blood pressure of the patient based on the first and second signals by evaluating the first signal in response to a maximum value of the second signal, the evaluating of the first signal including extracting a blood pressure waveform from the first signal, and
      shift the blood pressure waveform with respect to the first signal.

2. The system as claimed in claim 1, wherein the first sensing unit is a pressure cuff that includes a pressure sensor to provide the first signal.

3. The system as claimed in claim 1, wherein the second sensing unit includes an optical sensor.

4. The system as claimed in claim 1, wherein the second sensing unit includes a device for sensing an electrical characteristic of the patient or a pneumatic device.

5. A method of measuring blood pressure, comprising:
   sensing a first signal corresponding to a pressure;
   sensing a second signal corresponding to a blood flow;
   evaluating the first signal in response to a maximum value of the second signal to determine a first point; and
   determining a blood pressure based on the first and second signals and the first point, wherein determining the blood pressure based on the first point includes equating a systolic blood pressure to a measurement of the first signal at the first point.

6. The method as claimed in claim 5, wherein the first signal is sensed by a pressure sensing unit, the second signal is sensed by a blood flow sensing unit, and the pressure sensing unit and the blood flow sensing unit are placed proximate to one another.

7. The method as claimed in claim 6, wherein the pressure sensing unit is placed about at a base of a finger and the blood flow sensing unit is placed about at a tip of the finger.

8. The method as claimed in claim 5, wherein sensing the second signal comprises sensing the blood flow with an optical sensor.

9. The method as claimed in claim 5, wherein determining the blood pressure based on the first point comprises:
   extracting a third signal from the first signal, the third signal corresponding to changes in the blood pressure, and
   determining a systolic point in the third signal.

10. The method as claimed in claim 9, further comprising aligning the systolic point with the first point by shifting the third signal with respect to the first signal.

11. The method as claimed in claim 10, further comprising applying an oscillometric method to the third signal to calculate systolic and diastolic blood pressures after shifting the third signal.

12. The method as claimed in claim 9, further comprising applying an oscillometric method to the third signal to calculate systolic and diastolic blood pressures.

13. The method as claimed in claim 5, further comprising determining a diastolic blood pressure based on the calculation of the systolic blood pressure.

14. A method of measuring blood pressure, comprising:
   concurrently sensing a blood flow and a pressure;
   determining a maximum of the blood flow;
   determining a time at which the maximum in the blood flow occurred;
   comparing the maximum blood flow to the sensed pressure;
   determining a value of the sensed pressure at the time; and
   equating a systolic blood pressure to the value of the sensed pressure at the time.

15. The method as claimed in claim 14, wherein sensing the pressure comprises sensing a signal indicative of a pressure in a pressure pad.

16. The method as claimed in claim 14, wherein sensing the blood flow comprises sensing a signal provided by a blood flow sensor, the blood flow sensor adapted to attach to an appendage of a patient.

17. The system as claimed in claim 1, wherein the operation and control unit is further adapted to:
   determine a systolic point in the blood pressure waveform; and
   compare the systolic point with a first point, the first point being derived from the evaluation of the first signal in response to the maximum value of the second signal.

18. The system as claimed in claim 17, wherein shifting the blood pressure waveform with respect to the first signal includes aligning the systolic point with the first point.

19. The system as claimed in claim 18, wherein the operation and control unit is further adapted to apply an oscillometric method to the blood pressure waveform to calculate systolic and diastolic blood pressures after shifting the blood pressure waveform.

* * * * *